United States Patent
Song et al.

(10) Patent No.: US 11,266,674 B2
(45) Date of Patent: Mar. 8, 2022

(54) PHARMACEUTICAL COMPOSITION FOR TUMOR TREATMENT OR PREVENTION, METHOD, AND USE THEREOF

(71) Applicant: SICHUAN KELUN-BIOTECH BIOPHARMACEUTICAL CO., LTD., Sichuan (CN)

(72) Inventors: Hongmei Song, Sichuan (CN); Hong Zeng, Sichuan (CN); Xiaoda Niu, Sichuan (CN); Ying Wang, Sichuan (CN); Qiang Tian, Sichuan (CN); Daibiao Xiao, Sichuan (CN); Jiaqiang Cai, Sichuan (CN); Lichun Wang, Sichuan (CN); Jingyi Wang, Sichuan (CN)

(73) Assignee: SICHUAN KELUN-BIOTECH BIOPHARMACEUTICAL CO., LTD., Sichuan (CN)

( * ) Notice: Subject to any disclaimer, the term of this patent is extended or adjusted under 35 U.S.C. 154(b) by 93 days.

(21) Appl. No.: 16/627,897

(22) PCT Filed: Aug. 24, 2018

(86) PCT No.: PCT/CN2018/102242
§ 371 (c)(1),
(2) Date: Dec. 31, 2019

(87) PCT Pub. No.: WO2019/042226
PCT Pub. Date: Mar. 7, 2019

(65) Prior Publication Data
US 2020/0121707 A1    Apr. 23, 2020

(30) Foreign Application Priority Data
Sep. 1, 2017  (CN) .......................... 201710781366.0

(51) Int. Cl.
*A61K 31/7068*  (2006.01)
*A61P 35/00*    (2006.01)
*A61K 31/435*   (2006.01)
*C07K 16/28*    (2006.01)

(52) U.S. Cl.
CPC ........ *A61K 31/7068* (2013.01); *A61K 31/435* (2013.01); *A61P 35/00* (2018.01); *C07K 16/2827* (2013.01)

(58) Field of Classification Search
CPC .... A61K 31/7068; A61K 31/435; A61P 35/00
See application file for complete search history.

(56) References Cited

U.S. PATENT DOCUMENTS

| | | |
|---|---|---|
| 6,147,058 A | 11/2000 | Yoshimura et al. |
| 9,012,427 B2 | 4/2015 | Blatt et al. |
| 10,662,214 B2 * | 5/2020 | Ye .............................. C07H 1/00 |
| 2006/0142238 A1 | 6/2006 | McGuigan |
| 2014/0315850 A1 | 10/2014 | Huang et al. |
| 2014/0364446 A1 | 12/2014 | Dukhan et al. |
| 2018/0079770 A1 * | 3/2018 | Ye ............................ A61P 35/02 |
| 2018/0305464 A1 | 10/2018 | Li et al. |

FOREIGN PATENT DOCUMENTS

| | | |
|---|---|---|
| EP | 3 279 207 A1 | 2/2018 |
| WO | 2007/056596 A2 | 5/2007 |
| WO | 2012/045999 A1 | 4/2012 |
| WO | 2014/197578 A1 | 12/2014 |
| WO | 2016/068341 A1 | 5/2016 |
| WO | 2016/155593 A1 | 10/2016 |
| WO | 2016/189055 A1 | 12/2016 |

OTHER PUBLICATIONS

Sun (Lung Cancer, 93, 2016, 1-8).*
Brittain "X-Ray Diffraction of Pharmaceutical Materials", Profiles of Drug Substances, Excipients, and Related Methodology (2003), vol. 30, pp. 273-319.*
Ko et al., "Alteration of Amino Acid in Plasma and Cerebrospinal Fluid of Children with Seizure Disorders," *Kaohsiung J Med Sci* 9:131-142 (1993).
Supplementary European Search Report corresponding to EP Application No. 18 85 1571, 8 pages, dated Apr. 30, 2021.
International Search Report and Written Opinion, for International Application No. PCT/CN2018/102242, dated Nov. 12, 2018, 24 pages (with English translation).
Liu et al., "Fluorinated nucleosides: Synthesis and biological implication," *Journal of Fluorine Chemistry* 129',143-166, 2008.
Pradere et al., "Synthesis of Nucleoside Phosphate and Phosphonate Prodrugs," *Chem. Rev.* 114:9154-9218, 2014.
Slusarczyk et al., "Application of ProTide Technology to Gemcitabine: A Successful Approach to Overcome the Key Cancer Resistance Mechanisms Leads to a New Agent (NUC-1031) in Clinical Development," *J Med. Chem.* 57:1531-1542, 2014.
Tobias et al., "Synthesis and Biological Evaluation of a Cytarabine Phosphoramidate Prodrug," *Molecular Pharmaceutics* 1(2):112-116, 2004.
Yoshimura et al., "A Novel Synthesis of 2'-Modified 2'-Deoxy-4'-thiocytidines from $_D$-Glucose$^1$," *J. Org. Chem.* 62:3140-3152, 1997.
Yoshimura et al., "An Alternative Synthesis of the Antineoplastic Nucleoside 4'-ThioFAC and Its Application to the Synthesis of 4'-ThioFAG and 4'Thiocytarazid," *J. Org. Chem.* 64:19X2-1920, 1999.
Yoshimura et al., "Synthesis and Biological Activities of 2'-Deoxy-2'-fluoro-4'-thioarabinofuranosylpyrimidine and -Purine Nucleosides," *Bioogranic & Medicinal Chemistry* 8:1545-1558, 2000.

* cited by examiner

*Primary Examiner* — Pancham Bakshi
(74) *Attorney, Agent, or Firm* — Seed IP Law Group LLP

(57) ABSTRACT

A pharmaceutical composition comprising a 4'-thionucleoside phosphamide derivative or a pharmaceutically acceptable salt, ester, hydrate, solvate, and isomer thereof, any crystalline form thereof or racemate, metabolite, or a combination of a mixture thereof with other drugs, and a method and use thereof for disease treatment and/or prevention.

12 Claims, No Drawings

Specification includes a Sequence Listing.

PHARMACEUTICAL COMPOSITION FOR TUMOR TREATMENT OR PREVENTION, METHOD, AND USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 860245_401USPC_SEQUENCE_LISTING.txt. The text file is 6.7 KB, was created on Dec. 9, 2019, and is being submitted electronically via EFS-Web.

FIELD OF THE INVENTION

The present invention relates to a pharmaceutical composition comprising a 4'-thionucleoside phosphamide derivative, or a pharmaceutically acceptable salt, ester, hydrate, solvate, isomer, any crystalline form or racemate, metabolite thereof, or a mixture thereof, in combination with an additional drug, as well as a method and use thereof for disease treatment and/or prevention.

BACKGROUND OF THE INVENTION

A natural nucleoside is a glycoside comprising a ribose or a deoxyribose and a base (such as adenine, thymine, guanine, cytosine or uracil), and is an important component of DNA and RNA. Artificially synthesized nucleoside analogues are an important class of chemotherapeutic drugs for tumor, and are referred to as antimetabolites. The effect thereof is mainly achieved by interfering the synthesis of DNA in tumor cells. According to statistics from the WHO, cancer is one of the leading causes of death worldwide. Moreover, drug resistance in cancer cells is ubiquitous, and it is urgently needed to develop new anti-cancer drugs for human health. As such, it is an arduous task in the pharmaceutical industry to develop safe and reliable anti-cancer drugs from various perspectives.

WO2016155593 discloses 4'-thionucleoside phosphamide derivatives for the prevention or treatment of abnormal cell proliferative diseases, such as tumors or cancers and related disorders, or viral infectious diseases. The 4'-thionucleoside phosphamide derivatives are administered with orally good absorption, converted to active ingredients under the catalysis of corresponding enzymes, and interfere DNA synthesis in tumor cells, thereby resulting in tumor death.

In recent years, anti-tumor drugs such as kinase inhibitor drugs, biological macromolecules, and tumor immune small molecules etc. have been widely used in clinic. However, due to the diversity and mutation etc. features of tumor cell signaling pathways, problems such as prone to drug resistance, low effective response rate and poor single-use effect etc. exist in the application of the above-mentioned drugs. The survival rate of patients is difficult to be significantly improved when treated with a single drug. Currently, nucleoside drugs are still one of the main means of tumor chemotherapy, and play an important role in the treatment of some common tumors, such as lung cancer, breast cancer, colorectal cancer, and ovarian cancer, etc. However, conventional nucleoside drugs face drug resistance problems due to transporter variation and down regulation of phosphorylase. Novel nucleoside phosphamides can avoid such problems in conventional nucleoside drugs. Meanwhile, drug combination strategy based on novel nucleoside phosphamide drug candidates can significantly improve the effective rate and the survival rate of treatment, achieve the toxicity reducing and efficacy enhancing effect, and thus have wide clinical application value.

SUMMARY OF THE INVENTION

The present invention provides a method of treating and/or preventing tumor, comprising combined application or administration of therapeutically effective amounts of a 4'-thionucleoside phosphamide derivative, or a pharmaceutically acceptable salt, ester, hydrate, solvate, isomer, any crystalline form or racemate, metabolite thereof, or a mixture thereof, and one or more additional therapeutic agents. Preferably, the 4'-thionucleoside phosphamide derivative is the compound of formula (I) as described in WO2016/155593A1, which is incorporated herein by reference.

The present invention provides a method of manufacturing a medicament suitable for use in combination, comprising combining therapeutically effective amounts of a 4'-thionucleoside phosphamide derivative, or a pharmaceutically acceptable salt, ester, hydrate, solvate, isomer, any crystalline form or racemate, metabolite thereof, or a mixture thereof, and one or more additional therapeutic agents, so as to manufacture a medicament suitable for application or administration in combination for the prevention or treatment of an abnormal cell proliferative disease.

The present invention provides a method of preventing and/or treating an abnormal cell proliferative disease, comprising administering to a subject a therapeutically effective amount of a combination of a 4'-thionucleoside phosphamide derivative, or a pharmaceutically acceptable salt, ester, hydrate, solvate, isomer, any crystalline form or racemate, metabolite thereof, or a mixture thereof, and one or more additional therapeutic agents The present invention further provides the use of a 4'-thionucleoside phosphamide derivative, or a pharmaceutically acceptable salt, ester, hydrate, solvate, isomer, any crystalline form or racemate, metabolite thereof, or a mixture thereof, and one or more additional therapeutic agents in the manufacture of a medicament for the prevention and/or treatment of an abnormal cell proliferative disease The present invention provides a pharmaceutical composition comprising a 4'-thionucleoside phosphamide derivative, or a pharmaceutically acceptable salt, ester, hydrate, solvate, isomer, any crystalline form or racemate, metabolite thereof, or a mixture thereof, and one or more additional therapeutic agents, as well as a pharmaceutically acceptable carrier.

The present invention provides a pharmaceutical composition comprising a 4'-thionucleoside phosphamide derivative, or a pharmaceutically acceptable salt, ester, hydrate, solvate, isomer, any crystalline form or racemate, metabolite thereof, or a mixture thereof, and one or more additional therapeutic agents, as well as a pharmaceutically acceptable carrier, the pharmaceutical composition is preferably provided in the form of a kit.

DETAILED DESCRIPTION OF THE INVENTION

In some embodiments, the present invention provides use of a 4'-thionucleoside phosphamide derivative, or a pharmaceutically acceptable salt, ester, hydrate, solvate, isomer, any crystalline form or racemate, metabolite thereof, or a mixture thereof, and one or more additional therapeutic agents in the manufacture of a medicament for the prevention and/or treatment of an abnormal cell proliferative disease;

preferably, the 4'-thionucleoside phosphamide derivative has the structure of formula (I):

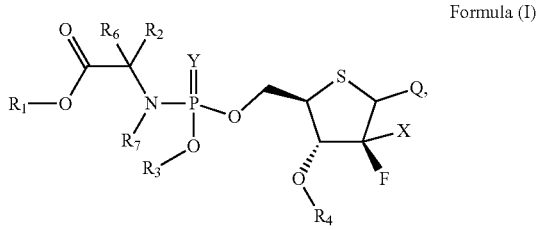

Formula (I)

wherein:

X is hydrogen, $C_{1-6}$ alkyl, halogen, $N_3$, OH, CN or SH;

Y is oxygen or sulfur;

$R_1$, $R_2$, $R_6$, and $R_7$ are each independently selected from the group consisting of hydrogen, optionally substituted $C_{1-10}$ alkyl, optionally substituted cycloalkyl, optionally substituted aryl, optionally substituted heterocyclyl, and optionally substituted heteroaryl, wherein $R_2$ and $R_6$ can be connected to form a 3-8 membered carbocyclic ring which may contain 0-3 heteroatoms selected from the group consisting of N, O, and S, and may be a saturated, unsaturated, or aromatic ring;

$R_3$ is selected from the group consisting of optionally substituted aryl and optionally substituted heteroaryl;

$R_4$ is selected from the group consisting of hydrogen, and optionally substituted $C_{1-10}$ acyl;

Q is a pyrimidine base or a purine base having the following structure:

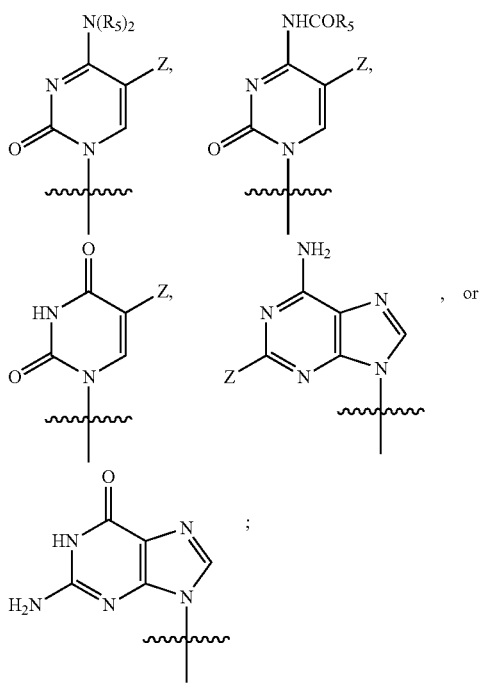

$R_5$, at each occurrence, is independently selected from the group consisting of hydrogen, optionally substituted $C_{1-10}$ alkyl and optionally substituted cycloalkyl; and Z is hydrogen, optionally substituted $C_{1-10}$ alkyl or halogen;

the above expression "optionally substituted" means unsubstituted or substituted with one or more substituents selected from the group consisting of halogen, alkyl, amino, alkylamino, alkoxy, haloalkyl, haloalkoxy, hydroxy, hydroxyalkyl, alkoxyalkyl, amido, sulfonamido, cyano, nitro, nitroso, azido, aldehyde, alkenyl, alkynyl, cycloalkyl, aryl, aralkyl, aryloxy, heteroaryl, heteroaryloxy, acyl, carboxyl, alkylcarbonyl, arylcarbonyl, heteroarylcarbonyl, and carboxylate; and the substituents can be connected to each other to form a 3-8 membered saturated, unsaturated or aromatic ring containing 0-3 heteroatoms selected from the group consisting of N, O, and S.

In certain embodiments, the additional therapeutic agent includes, but is not limited to, an anti-tumor agent.

In certain embodiments, the anti-tumor agent includes, but is not limited to, a cytotoxic anti-tumor agents, agents affecting endocrine balance, biological response modifier agents, anti-tumor antibody agents, small molecule kinase inhibitor anti-tumor agents, and other adjunctive therapeutic agents.

In certain embodiments, the cytotoxic anti-tumor agent includes, but is not limited to, chlormethine, cyclophosphamide, glyfosfin, cisplatin, oxaliplatin, carboplatin, iproplatin, nedaplatin, lobaplatin, doxorubicin, pirarubicin, mitomycin, bleomycin, actinomycin-D, aclarubicin, methotrexate, fluorouracil, hydroxycarbamide, cytarabine, gemcitabine, azacytidine, fludarabine, nelarabine, forodesine, cladribine, clofarabine, capecitabine, mercaptopurine, vincristine, paclitaxel, homoharringtonine, asparaginase, irinotecan, etoposide, tretinoin, and bortezomib.

In certain embodiments, the agent affecting endocrine balance includes, but is not limited to, tamoxifen, toremifene, flutamide, letrozole, exemestane, medroxyprogesterone, megestrol, goserelin, triptorelin and the like.

In certain embodiments, the biological response modifier agent includes, but is not limited to, interleukin-2, thymopeptide, interferon, adenovirus P53 and the like.

In certain embodiments, the anti-tumor antibody agent includes, but is not limited to, trastuzumab, rituximab, cetuximab, bevacizumab, nimotuzumab, human endostatin, recombinant human 5 adenovirus, recombinant human tumor necrosis factor, recombinant human P53 adenovirus, iodine (131I) metuximab, nivolumab (Opdivo), pembrolizumab, Atezolizumab, Avelumab, and PDL-1 antibody.

In certain embodiments, the small molecule kinase inhibitor anti-tumor agent includes, but is not limited to, reversible non-receptor tyrosine kinase (NRTK) inhibitor anti-tumor agents, reversible receptor tyrosine kinase (RTK) inhibitor anti-tumor agents, irreversible protein kinase inhibitor anti-tumor agents, serine/threonine kinase inhibitor anti-tumor agents, and lipid kinase inhibitor anti-tumor agents.

In certain embodiments, the reversible non-receptor tyrosine kinase (NRTK) inhibitor anti-tumor agent includes, but is not limited to, sunitinib malate, dasatinib, nilotinib hydrochloride, bosutinib, ponatinib hydrochloride, ruxolitinib phosphate and tofacitinib citrate.

In certain embodiments, the reversible receptor tyrosine kinase (RTK) inhibitor anti-tumor agent includes, but is not limited to, gefitinib, nilotinib, lapatinib, vandetanib, afatinib, osimertinib, sorafenib, pazopanib, axitinib, regorafenib, nintedanib, lenvatinib, crizotinib, ceritinib, cabozantinib, and alectinib.

In certain embodiments, the irreversible protein kinase inhibitor anti-tumor agent includes, but is not limited to, ibrutinib.

In certain embodiments, the serine/threonine kinase inhibitor anti-tumor agent includes, but is not limited to, vemurafenib, dabrafenib mesylate, trametinib dimethyl sulfoxide, cobimetinib, and palbociclib.

In certain embodiments, the lipid kinase inhibitor anti-tumor agent includes, but is not limited to, idelalisib.

In certain embodiments, the other adjunctive therapeutic agent includes, but is not limited to, recombinant human granulocyte colony-stimulating factor, erythropoietin, interleukin D11, indomethacin, tramadol, morphine, domperidone, granisetron, tropisetron, pamidronate disodium, and zoledronic acid.

In certain embodiments, the additional therapeutic agent is Sorafenib or a PDL-1 antibody.

The PDL-1 antibody as described in the present invention is a monoclonal antibody against the PDL-1 target, such as MPDL3280A, Durvalumab (MEDI4736), Durvalumab, MSB0010718C, AMP224, RG7446, Atezolizumab (trade name Tecentriq®), PCAB or the PDL-1 monoclonal antibodies described in Chinese patent application No. 201710120847.7 etc.

The PDL-1 antibody as described in the present invention is preferably selected from the monoclonal antibodies described in Chinese patent application No. 201710120847.7, which is incorporated herein by reference in its entirety. These PDL-1 antibodies can efficiently and specifically bind to PDL-1, effectively blocks the binding of PD-1 with PDL-1, and specifically relieve the immunosuppression of PDL-1 to the body, thereby activating T lymphocytes. The PDL-1 antibody is preferably selected from the monoclonal antibodies having the following combinations of a heavy chain variable region and a light chain variable region: SEQ ID NO:1 and SEQ ID NO:2, SEQ ID NO:3 and SEQ ID NO:4, SEQ ID NO:3 and SEQ ID NO:6, SEQ ID NO:5 and SEQ ID NO:4, and SEQ ID NO:5 and SEQ ID NO:6.

As an example, the PDL-1 antibody is selected from the group consisting of 5C10, 5C10H1L1, 5C10H1L2, 5C10H2L1 and 5C10H2L2 monoclonal antibodies described in Chinese patent application No. CN 201710120847.7. The heavy chain variable region and the light chain variable region of 5C10 are respectively SEQ ID NO:1 and SEQ ID NO:2; the heavy chain variable region and the light chain variable region of 5C10H1L1 are respectively SEQ ID NO:3 and SEQ ID NO:4; the heavy chain variable region and the light chain variable region of 5C10H1L2 are respectively SEQ ID NO:3 and SEQ ID NO:6; the heavy chain variable region and the light chain variable region of 5C10H2L1 are respectively SEQ ID NO:5 and SEQ ID NO:4; and the heavy chain variable region and the light chain variable region of 5C10H2L2 are respectively SEQ ID NO:5 and SEQ ID NO:6.

In certain embodiments, the PDL-1 antibody comprises a mutated human IgG1 constant region, wherein the heavy chain constant region comprises an N297A mutation according to the EU numbering system.

In certain embodiments, the mutated human IgG1 constant region in the antibody comprises, or further comprises, 1, 2 or 3 mutations of L234A, L235A or G237A at positions 234, 235 and 237 in the heavy chain constant region according to the EU numbering system.

In certain embodiments, the 4'-thionucleoside phosphamide derivative is preferably the compound of formula (I) as described in WO2016/155593A1, the disclosure of which is incorporated herein by reference in its entirety, preferably the 4'-thionucleoside phosphamide derivative of formulae C1-C19 as described in WO2016/155593A1, and the particularly preferred compound is selected from the group consisting of the compounds represented by the following formulae:

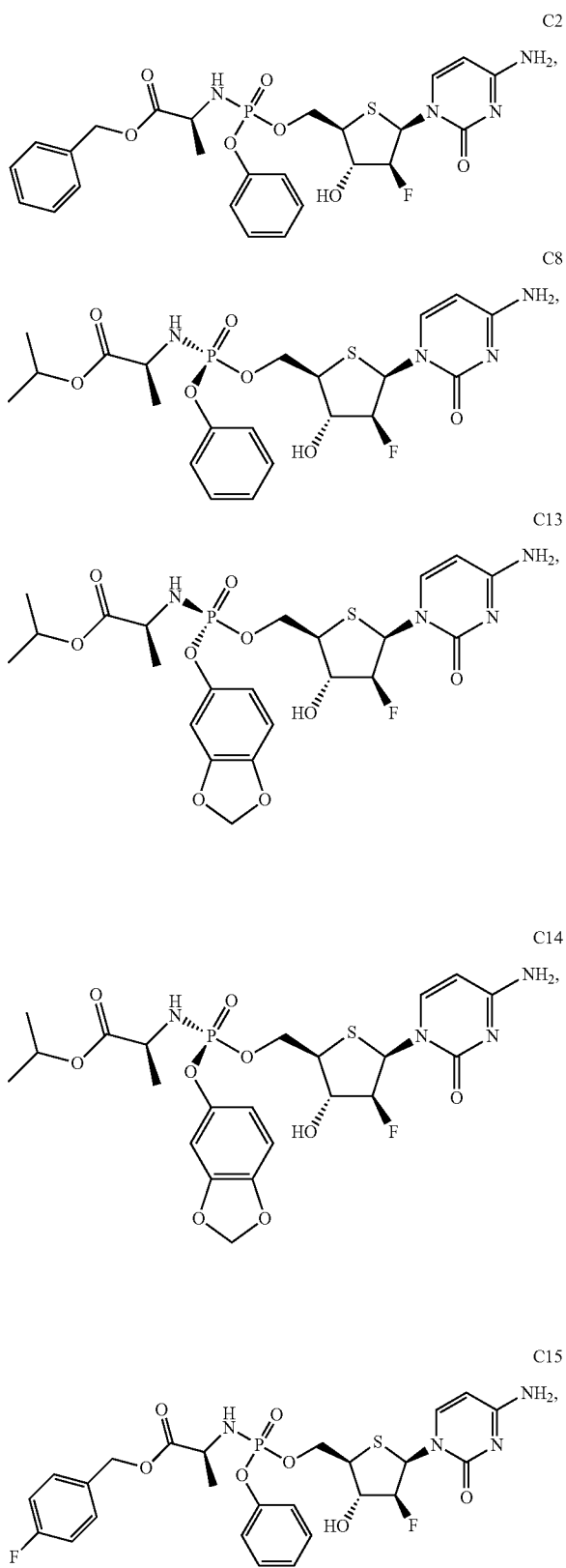

C16
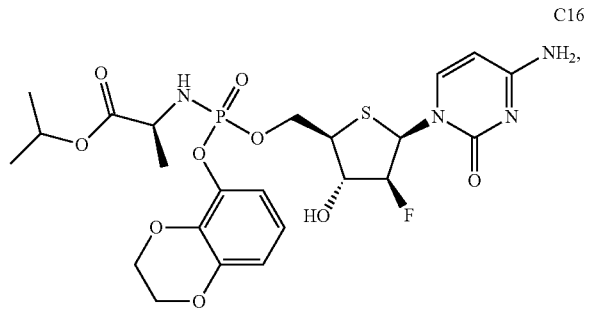

C17
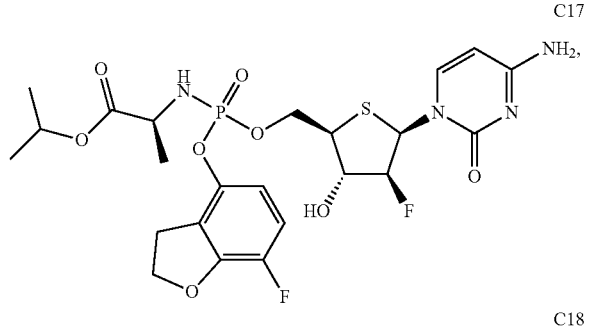

C18 and
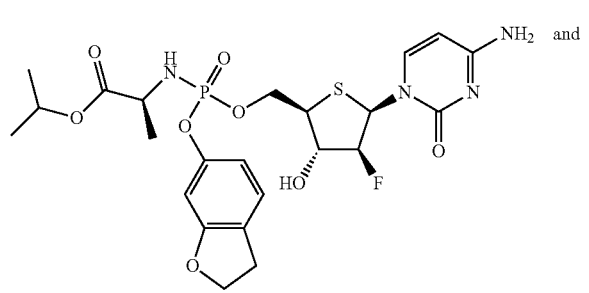

C19
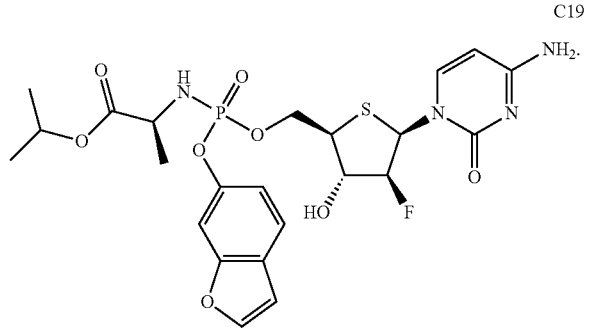

In certain embodiments, the abnormal cell proliferative disease comprises cancers in esophagus, stomach, intestine, rectum, mouth, pharynx, larynx, lung, colon, breast, uterus, endometrium, ovary, prostate, testis, bladder, kidney, liver, pancreas, bone, connective tissue, skin, eye, brain and central nervous system, as well as thyroid cancer, leukemia, Hodgkin disease, lymphoma and myeloma.

In preferred embodiments, the abnormal cell proliferative disease is preferably liver cancer or lung cancer; and the lung cancer is preferably non-small cell lung cancer.

As an example, the 4'-thionucleoside phosphamide derivative in the present invention, e.g., compound C2, C13, C14, C15, C16, C17, C18, or C19, is combined with Sorafenib for the treatment of liver cancer; alternatively, any of the above 4'-thionucleoside phosphamide derivative can be combined with a PDL-1 antibody (e.g., 5C10, 5C10H1L1, 5C10H1L2, 5C10H2L1, and 5C10H2L2) for treatment of lung cancer, e.g., non-small cell lung cancer.

In certain embodiments, the medicament in the present invention comprises one or more dosage units of the 4'-thionucleoside phosphamide derivative and one or more additional therapeutic agents, and the medicament is for administration to a mammal (preferably human) in need thereof, wherein the 4'-thionucleoside phosphamide derivative, or a pharmaceutically acceptable salt, ester, hydrate, solvate, isomer, any crystalline form or racemate, metabolite thereof, or a mixture thereof and one or more additional therapeutic agents in the medicament can be present in a same dosage unit or different dosage units, and when in different dosage units, they are used simultaneously, sequentially or alternately.

In certain embodiments, the weight ratio between the 4'-thionucleoside phosphamide derivative in the present invention, or a pharmaceutically acceptable salt, ester, hydrate, solvate, isomer, any crystalline form or racemate, metabolite thereof, or a mixture thereof and the one or more additional therapeutic agents is 1:(1-50), preferably 1:(1-30), preferably 1:(1-20), preferably 1:(5-20), further preferably 1.5:10, 1.5:20 or 1.5:30.

In certain embodiments, the present invention provides a method of preventing and/or treating an abnormal cell proliferative disease, comprising administering to a subject a therapeutically effective amount of a combination of a 4'-thionucleoside phosphamide derivative, or a pharmaceutically acceptable salt, ester, hydrate, solvate, isomer, any crystalline form or racemate, metabolite thereof, or a mixture thereof, and one or more additional therapeutic agents.

In certain embodiments, the present invention provides a pharmaceutical composition comprising a 4'-thionucleoside phosphamide derivative, or a pharmaceutically acceptable salt, ester, hydrate, solvate, isomer, any crystalline form or racemate, metabolite thereof, or a mixture thereof, and one or more additional therapeutic agents, as well as a pharmaceutically acceptable carrier, and the pharmaceutical composition is preferably provided in the form of a kit.

In preferred embodiments, the kit comprises (a) a first component in a first container, the first component being a 4'-thionucleoside phosphamide derivative, or a pharmaceutically acceptable salt, ester, hydrate, solvate, isomer, any crystalline form or racemate, metabolite thereof, or a mixture thereof, and a pharmaceutically acceptable carrier; (b) a second component in a second container, the second component being one or more additional therapeutic agents and a pharmaceutically acceptable carrier; and (c) an optional instruction.

In certain embodiments, the first component and the second component are administered by the same route (e.g., oral) or different routes (e.g., oral and parenteral (e.g., injection) administration).

In certain embodiments, the first component and the second component are administered simultaneously, sequentially or alternately.

In certain embodiments, the first component and the second component are administered at different dosing intervals, and the dosage of any component can be increased gradually according to the discretion of the prescribing physician.

In certain embodiments, the first component and the second component are administered at a dosing interval of longer than 4 h.

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that most of the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "combined application" or "combined administration" comprises the simultaneous, sequential, alternative use of two or more drugs or pharmaceutical components, including the formulation of two or more drugs or pharmaceutical components in one or more dosage units, so as to obtain a pharmaceutical product suitable for combined administration, and the pharmaceutical product is administered to a mammal in need of combined administration. In preferred embodiments, the pharmaceutical product is provided in the form of a kit.

The medicament or pharmaceutical composition of the present invention may be in the form of a solid preparation, a semi-solid preparation, a liquid preparation or a gas preparation, etc. For example, the solid preparation is a tablet, capsule, powder, granule or suppository etc., and the liquid preparation is a solution, suspension or injection. The medicament or pharmaceutical composition may also be in the dosage form of liposome, microsphere or the like. In particular, the medicament or pharmaceutical composition is in a dosage form suitable for oral administration, or for administration by injection.

As used herein, the term "pharmaceutically acceptable carrier" refers to a non-active ingredient in a pharmaceutical composition or pharmaceutical formulation that does not cause significant irritation to an organism and does not substantially affect the biological activity of the active ingredient being administered, and includes, for example, diluents, adjuvants, excipients, or suitable pharmaceutically acceptable vehicles. Examples of suitable pharmaceutically acceptable carriers are described, for example, in Remington's Pharmaceutical Sciences (1990).

As used herein, the term "metabolite" or "metabolic form" refers to a compound generated in vivo after a drug is applied to a subject in need thereof.

As used herein, the term "pharmaceutically acceptable salt" refers to those salts which retain the biological effectiveness etc. of the parent compound or drug, and can be prepared in the following manner: a proton-accepting moiety is partially protonated and/or a proton-donating moiety is partially deprotonated. It should be noted that the partial protonation of the proton-accepting moiety results in a cationic species, the charge of which is balanced by the presence of a physiological anion, while the partial deprotonation of the proton-donating moiety results in an anionic species, the charge of which is balanced by the presence of a physiological cation.

A pharmaceutically acceptable salt of the compound, derivative, medicament or active ingredient in the present invention includes an acid addition salt and a base addition salt thereof.

A suitable acid addition salt can be formed from a suitable pharmaceutically acceptable acid and includes an inorganic acid and an organic acid. In the present invention, a suitable inorganic acid is an acid as defined in the field of chemistry, such as hydrochloric acid, sulfuric acid or phosphoric acid, etc. A suitable organic acid includes an organic sulfonic acid, an organic carboxylic acid, or an amino acid, etc. A suitable organic sulfonic acid is e.g. $C_{6-16}$ aryl sulfonic acid, $C_{6-16}$ heteroaryl sulfonic acid, or $C_{1-16}$ alkyl sulfonic acid, and a suitable organic carboxylic acid is e.g. monocarboxylic acid or polycarboxylic acid, including $C_{1-16}$ alkyl carboxylic acid, $C_{6-16}$ aryl carboxylic acid and $C_{4-16}$ heteroaryl carboxylic acid. The organic carboxylic acid can also be e.g. an amino acid, various kinds of which are suitable, particularly natural amino acids which are found as components of proteins. Specific examples of salts formed from the above acids include the acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

A suitable base addition salt is formed from a base which forms non-toxic salts and includes an inorganic base and an organic base. Specific examples include the aluminum, arginine, benzathine, calcium, choline, diethylamine, diolamine, glycine, lysine, magnesium, meglumine, olamine, potassium, sodium, tromethamine and zinc salts.

The medicament or the component (e.g., the 4'-thio-nucleoside phosphamide derivative and/or the additional therapeutic agent) in the medicament of the present invention can exist as a hydrate, or as a solvate, wherein the medicament or the active ingredient of the present invention contains a solvent, in particular water, methanol or ethanol for example as a structural element of the crystal lattice of the compound.

The present invention includes all possible crystalline forms, or polymorphs, of the medicament of the present invention, either as a single polymorph, or as a mixture of more than one polymorphs, in any ratio.

As used herein, the term "excipient" refers to a substance for the preparation of a medicament or a pharmaceutical composition, and it is generally safe, and neither biologically nor otherwise undesirable, and includes various excipients suitable for veterinary use as well as human pharmaceutical use.

The pharmaceutically acceptable carrier which can be employed in the medicament or the pharmaceutical composition of the present invention includes, but is not limited to sterile liquids, such as water and oils, including those of petroleum, animal, vegetable or synthetic origin, such as peanut oil, soybean oil, mineral oil, sesame oil and the like.

Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The medicament or the pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc.

As used herein, the term "formulation" or "dosage form" shall include solid, semi-solid, liquid, or gas formulations. The formulation or dosage form includes, but is not limited to, tablets, capsules, lozenges, hard candies, powders, sprays, creams, salves, suppositories, gels, pastes, lotions, ointments, aqueous suspensions, injectable solutions, elixirs, syrups, and the like. Those skilled in the art will appreciate that, depending on the desired dose and pharmacokinetic parameters, the compound of the present invention may be prepared as different formulations.

The unit dosage range of the active ingredient in the medicament of the present invention is 0.1-1000 mg, preferred unit dosage range is 1-800 mg, more preferred unit dosage range is 10-600 mg, particularly preferred unit dosage range is 50-450 mg, and the most preferred unit dosage range is 100-300 mg.

In certain embodiments, the unit dosage of a pharmaceutically active ingredient (e.g., a 4'-thionucleoside phosphamide derivative, or an additional therapeutic agent such as Sorafenib, PDL-1 antibody or the like) is administered in the amount of about 1 mg, about 2 mg, about 3 mg, about 4 mg, about 5 mg, about 6 mg, about 7 mg, about 8 mg, about 9 mg, about 10 mg, about 25 mg, about 50 mg, about 75 mg, about 100 mg, about 150 mg, about 200 mg, about 250 mg, about 300 mg, about 350 mg, about 400 mg, about 500 mg, or about 600 mg.

The formulation or dosage form of the present invention may contain a single or multiple unit dosages as above of the pharmaceutically active ingredient in the present invention.

In certain embodiments, the active ingredient PDL-1 antibody is administered parenterally. In certain embodiments, the PDL-1 antibody is administered in an amount of about 0.5 mg/Kg (about 0.5 mg anti-PDL-1 monoclonal antibody per kilogram of the subject's weight), about 1 mg/Kg, about 2 mg/Kg, about 3 mg/Kg, about 4 mg/Kg, about 5 mg/Kg, about 6 mg/Kg, about 7 mg/Kg, about 8 mg/Kg, about 9 mg/Kg, about 10 mg/Kg, about 11 mg/Kg, about 12 mg/Kg, about 13 mg/Kg, about 14 mg/Kg, about 15 mg/Kg, about 16 mg/Kg, about 17 mg/Kg, about 18 mg/Kg, about 19 mg/Kg, or about 20 mg/Kg. In a particular embodiment, the PDL-1 antibody is administered intravenously in a dosage amount as described above.

In certain embodiments, the medicament or the pharmaceutically active ingredient in the present invention is for oral administration. In various situations, other administration routes may be employed or even preferred, such as intravenous, intraarterial, subcutaneous, intraperitoneal, intramuscular, or transdermal administration, or administration via buccal, nasal, transmucosal, topical, route, as an ophthalmic formulation, or via inhalation. Transdermal administration may be very desirable for patients who are forgetful or petulant about taking oral medicine. The compound of the present invention may also be administered by the percutaneous, intramuscular, intranasal or intrarectal route in particular circumstances. The route of administration may be varied in any way, depending on the physical properties of the medicament or the pharmaceutically active ingredient, the convenience of the patient and the caregiver, and other relevant conditions (Remington's Pharmaceutical Sciences, 18th Edition, Mack Publishing Co. (1990)).

The dosage range of the active ingredient of the present invention or a product comprising the same (such as a medicament, a pharmaceutical composition, a pharmaceutical formulation, or a dosage form) is 0.1-1000 mg/kg body weight per day, preferred dosage range is 0.1-800 mg/kg body weight per day, preferred dosage range is 1-600 mg/kg body weight per day, preferred dosage range is 10-400 mg/kg body weight per day, particularly preferred dosage range is 50-300 mg/kg body weight per day, and the most preferred dosage range is 100-250 mg/kg body weight per day. The exact dosage required for treating a patient may be determined by a physician in view of the stage and severity of the disease as well as patient's specific need and response.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "PDL-1" may also be referred to as "Programmed death-ligand 1", "Programmed cell death ligand 1", "protein PD-L1", "PD-L1", "PDL1", "PDCDL1", "hPD-L1", "hPD-Ll", "CD274" and "B7-H1", and they can be used interchangeably.

The term "antibody" as used herein is used in the broadest sense and covers complete monoclonal antibodies, polyclonal antibodies, and multispecific antibodies formed from at least two complete antibodies (e.g., bispecific antibodies), so long as they exhibit the desired biological activity. As used herein, "antibody" and "immunoglobulin" can be used interchangeably.

The term "monoclonal antibody" as used herein refers to an antibody obtained from a population of substantially homogeneous antibodies, i.e., the individual antibodies constituting the population are identical except for possible naturally occurring mutations that may be present in minor amounts. Monoclonal antibodies are highly specific to a single antigenic determinant (epitope), and in contrast, polyclonal antibodies include different antibodies directed against different determinants (epitopes). Besides specificity, monoclonal antibodies are advantageous in that they can be synthesized without contamination by other antibodies. Here the modifier "monoclonal" indicates the character of the antibody as being obtained from a substantially homogeneous population of antibodies, and is not to be construed as requiring any particular production method.

In certain embodiments of the present invention, the monoclonal antibodies specifically include chimeric antibodies in which a portion of the heavy and/or light chain is identical or homologous to corresponding sequences in antibodies of a certain species, a certain class, or a certain subclass, while the remainder of the chain(s) is identical or homologous to corresponding sequences in antibodies of another species, another class, or another subclass, so long as they exhibit the desired biological activity (see e.g. U.S. Pat. No. 4,816,567; and Morrison et al., (1984) Proc. Natl. Acad. Sci. USA, 81: 6851-6855). Chimeric antibodies that can be used in the present invention include primatized antibodies comprising variable domain antigen-binding sequences from a non-human primate (e.g., old world monkey, gorilla, etc.) and human constant region sequences.

As used herein, the term "antibody fragments" refers to a portion of an antibody, preferably the antigen-binding or variable region thereof. Examples of antibody fragments include Fab, Fab', F(ab')$_2$, Fd, Fv, dAb and complementary determining region fragments; diabodies; linear antibodies; and single-chain antibody molecules.

In the present invention, "humanized" forms of non-human (e.g., mouse) antibodies refer to chimeric antibodies that contain minimal sequence derived from non-human immunoglobulin. Most humanized antibodies are human immunoglobulins (donor antibody) in which residues from a hypervariable region are replaced by residues from a hypervariable region of a non-human (e.g., mouse, rat, rabbit or nonhuman primate) species (donor antibody) having the desired specificity, affinity, and capacity. In some embodiments, framework region (FR) residues of the human immunoglobulin are also replaced by non-human residues. Furthermore, humanized antibodies may comprise residues that are not found in the recipient antibody or in the donor antibody. These modifications are made to further refine antibody performance. A humanized antibody generally comprises at least one, and typically two variable domains, in which all or substantially all of the hypervariable loops correspond to those of a non-human immunoglobulin, and all or substantially all of the FRs are those of a human immunoglobulin sequence. The humanized antibody can also comprise at least a portion of an immunoglobulin constant region (Fc, typically Fc of a human immunoglobulin). For details, see e.g., Jones et al., 1986, Nature, 321: 522-525; Riechmann et al., 1988, Nature, 332: 323-329; and Presta, 1992, Curr. Op. Struct. Bwl 2: 593-596.

Depending on the amino acid sequence of the constant domain of their heavy chains, intact antibodies can be assigned to different "classes". The five major classes are IgA, IgD, IgE, IgG, and IgM, and several of these may be further divided into "subclasses" (isotypes), e.g., IgG1, IgG2, IgG3, IgG4, IgA1, and IgA2. The heavy-chain constant domains of different classes of antibodies are known as α, δ, ε, γ, and μ, respectively. The subunit structures and three-dimensional configurations of different classes of immunoglobulins are well known in the art.

Monoclonal antibodies used in the present invention can be produced by various methods. For example, monoclonal antibodies for use in the present invention can be obtained by a hybridoma method using various species (including cells of mice, hamsters, rats and human) (see e.g., Kohler et al., 1975, Nature, 256: 495), or by a recombinant DNA technology (see e.g., U.S. Pat. No. 4,816,567), or by isolation from phage antibody libraries (see e.g., Clackson et al., 1991, Nature, 352: 624-628; and Marks et al., 1991, Journal of Molecular Biology, 222: 581-597).

As used herein, the term "mammal" includes a human or non-human animal. An exemplary human subject includes a human subject having a disease or disorder (such as one described herein) (referred to as a patient), or a normal subject. The term "non-human animal" as used herein includes non-human primates, livestock and/or domesticated animals, such as sheep, dog, cat, cow, pig and the like.

As used herein, the term "container" is a container for containing a pharmaceutical component. This container can be used for preparation, storage, transportation, and/or stand-alone/bulk sale, and is intended to encompass a bottle, jar, vial, flask, syringe, tube (e.g., for a cream preparation), or any other containers for preparing, containing, storing, or dispensing a pharmaceutical product.

As used herein, the term "instruction" is a trademark, tag, label, or the like, which lists information relating to the pharmaceutical component in the container. The listed information is typically determined by a regulatory agency governing the area where the article is to be sold, such as the U.S. Food and Drug Administration. Preferably, the package instruction specifically lists the indications for which the pharmaceutical component is approved. The package instruction can be made of any material from which information contained therein or thereon can be read. Preferably, the package instruction is a printable material (e.g., paper, plastic, cardboard, foil, adhesive paper or plastic, etc.) on which the desired information can be formed (e.g., printed or applied).

Technical Effect

An advantageous effect was achieved by employing the 4'-thionucleoside phosphamide derivative together with an additional therapeutic agent in the present invention for preventing and/or treating an abnormal cell proliferative disease. The results showed that compared with the groups treated with a single drug, the group treated with a drug combination exhibited a better therapeutic effect, where a synergistic effect was achieved and good tolerance was shown.

EXAMPLES

The present invention is further illustrated by the following description of specific embodiments, which by no means limits the invention. Various modifications or improvements can be made by those skilled in the art in light of the teachings of this invention without departing from the basic spirit and scope of the present invention.

In the examples of the present invention, compound C8 in WO2016/155593A1 was used as the 4'-thionucleoside phosphamide derivative compound.

Example 1: In Vivo Efficacy on Subcutaneous Xenograft of Human Hepatoma Hep3B Cells This example aimed to evaluate the in vivo efficacy and tolerability of the pharmaceutical combination of the present invention in a NU/NU nude mouse model with human hepatoma Hep3B cell subcutaneous xenografts.

1. Cell Line for the Test

Human hepatoma Hep3B cells were cultured as a monolayer in vitro, and the culture conditions were EMEM culture medium supplemented with 10% Fetal Bovine Serum, and incubation in an incubator at 37° C. and 5% $CO_2$. The cells were subcultured by treatment with routine trypsin-EDTA digestion twice a week.

2. Tumor Cell Inoculation and Grouping of Animals 0.2 mL of a cell suspension (PBS:Matrigel=1:1) containing $1 \times 10^6$ Hep3B was inoculated subcutaneously into the right flank of each mouse. After the inoculated tumor reached an average size in the range of 100-200 mm$^3$, the grouping of animals was performed.

3. Sample Preparation 5 g of sodium carboxymethyl cellulose was weighed and placed in a 1000 mL wide-mouth bottle, 800 mL of ultrapure water was added, and the mixture was stirred to effect a solution, the volume of which was then filled up to 1000 mL, thereby obtaining the vehicle.

An appropriate amount of the 4'-thionucleoside phosphamide derivative compound in the present invention was weighed, a certain amount of the vehicle was added, and a uniform suspension was obtained after mixing.

An appropriate amount of Sorafenib was weighed, and dissolved by adding polyoxyethylene castor oil. Ethanol was added and evenly mixed, followed by addition of physiological saline, thereby obtaining a uniform suspension.

4. Test Method

Mice bearing a tumor having a volume of 100-200 mm$^3$ were selected, and randomized into groups (8 mice per group). The dosing volume was 10 mL/kg (in the group treated with the drug combination, the two drugs were administered individually at an interval of 4 hours), and the administration was performed by oral gavage (p.o.) every day for 20 days. The tumor volume, body weight of the animals and tumor weight were measured.

5. Test Indexes (1) The Anti-Tumor Effect was Evaluated by Measuring the Tumor Volume.

The equation for calculating the tumor volume is as follows: $V=0.5 a \times b^2$, wherein a and b respectively represent the major and minor diameters of a tumor.

Relative Tumor Volume (RTV):

$RTV=V_t/V_0$; wherein $V_0$ is the average tumor volume measured at the time of grouping for administration (i.e., Day 0); and $V_t$ is the average tumor volume measured on Day t.

The anti-tumor efficacy was evaluated by tumor growth inhibition $TGI_{volume}$ (%) and $T/C_{volume}$ (%). $T/C_{volume}$ (%)=$T_{RTV}/C_{RTV} \times 100\%$; $TGI_{volume}$ (%)=$100\%-T/C_{volume}$ (%); wherein $T_{RTV}$ and $C_{RTV}$ are respectively RTVs of the treatment group and vehicle group at the end of the test.

(2) The Animal's Tolerance to a Drug was Evaluated by Animal Body Weight Change.

The method for calculating the animal body weight change (%) is as follows: $(W_t-W_0)/W_0 \times 100\%$; $W_0$: the animal's body weight at the time of grouping for administration (i.e., Day 0); $W_t$: the animal's body weight on day t of the test.

(3) The Anti-Tumor Effect was Evaluated by Tumor Weight.

$TGI_{tumor\ weight}$ (%) and $T/C_{tumor\ weight}$ (%) were calculated based on tumor weight, and were used to evaluate the tumor inhibitory effect. The equation for calculation is as follows:

$$T/C_{tumor\ weight}(\%)=W_{Tt}/W_{Ct} \times 100\%;$$

$$TGI_{tumor\ weight}(\%)=100\%-T/C_{tumor\ weight}(\%);$$

$W_{Tt}$ is the average tumor weight in the treatment group at the end of the test; and $W_{Ct}$ is the average tumor weight in the vehicle group at the end of the test.

(4) Criteria for Determining Synergism

The synergism was evaluated by Jin's equation $q=E_{A+B}/(E_A+E_B-E_A \times E_B)$, wherein $E_{A+B}$ represents the efficacy achieved by the combination, and $E_A$ or $E_B$ represents the efficacy achieved by individual administration. In the present invention, the efficacy indicated in the equation refers to TGI %. When q<0.85, the combination administration is considered to achieve an antagonistic effect; when q=0.85-1.15, the combination administration is considered to achieve an additive effect; and when q>1.15, the combination administration is considered to achieve a synergistic effect.

6. Test Results 6.1 Body Weight Change

Body weight change in the animals tested serve as a reference indicator for determining drug tolerance.

The test results are shown in Table 1. On Day 20 of the treatment, the 4'-thionucleoside phosphamide derivative compound in the present invention resulted in an increase in the body weight of the Hep3B cell tumor-bearing mice by 1.20% at a dosage of 1.5 mg/kg. Sorafenib, however, caused certain weight loss at the dosage of 30 mg/kg, which was 8.31%. When the 4'-thionucleoside phosphamide derivative compound in the present invention at a dosage of 1.5 mg/kg was administered in combination with Sorafenib at a dosage of 30 mg/kg, the Hep3B cell tumor-bearing mice showed good tolerance with a weight gain of 0.42%. As such, the combination of the 4'-thionucleoside phosphamide derivative compound in the present invention and Sorafenib addressed the issue of weight loss caused by Sorafenib, which is unexpected.

TABLE 1

Weight change of the Hep3B cell tumor-bearing mice in each of the groups

| Group | Dosage (mg/kg) | Administration route | Body weight change (%) |
|---|---|---|---|
| The 4'-thionucleoside phosphamide derivative compound in the present invention | 1.5 | p.o. | ±1.20% |
| Sorafenib | 30 | p.o. | −8.31% |
| The 4'-thionucleoside phosphamide derivative compound in the present invention + Sorafenib | 1.5 + 30 | p.o. | ±0.42% |

Note: error range: ±0.2%

6.2 Tumor Volume Change

The test results are shown in Table 2. On Day 20 of the treatment, the average tumor volume was 1,390.38 mm³ and the tumor growth inhibition rate ($TGI_{volume}\%$) was 34.75% ($T/C_{volume}\%$=65.25%, p=0.57) when the 4'-thionucleoside phosphamide derivative compound in the present invention was administered alone at a dosage of 1.5 mg/kg; while the average tumor volume was 912.68 mm³ and the tumor growth inhibition rate ($TGI_{volume}\%$) was 57.14% ($T/C_{volume}\%$=42.86%, p=0.08) when Sorafenib was administered alone at a dosage of 30 mg/kg.

When the 4'-thionucleoside phosphamide derivative compound in the present invention at a dosage of 1.5 mg/kg was administered in combination with Sorafenib at a dosage of 30 mg/kg for 20 days, the average tumor volume was 125.25 mm³, and the tumor growth inhibition rate ($TGI_{volume}\%$) was as high as 94.13% ($T/C_{volume}\%$=5.87%, p<0.01). The q value calculated according to the Jin's equation was 1.31, indicating that the combination of the two drugs achieved a significant synergistic effect.

TABLE 2

Evaluation of the anti-tumor efficacy on Hep3B xenograft

| Group | Dosage mg/kg | Tumor volume (mm³) | | $TGI_{volume}$ (%) | $T/C_{volume}$ (%) | p value | q value |
|---|---|---|---|---|---|---|---|
| | | Day 0 | Day 20 | | | | |
| Vehicle group | — | 137.22 ± 6.67 | 2129.53 ± 346.77 | — | — | — | — |
| The 4'-thionucleoside phosphamide derivative compound in the present invention | 1.5 | 137.67 ± 7.75 | 1390.38 ± 275.59 | 34.75 | 65.25 | 0.57 | — |

TABLE 2-continued

Evaluation of the anti-tumor efficacy on Hep3B xenograft

| Group | Dosage mg/kg | Tumor volume (mm³) Day 0 | Tumor volume (mm³) Day 20 | $TGI_{volume}$ (%) | $T/C_{volume}$ (%) | p value | q value |
|---|---|---|---|---|---|---|---|
| Sorafenib | 30 | 137.77 ± 7.92 | 912.68 ± 173.12 | 57.14 | 42.86 | 0.08 | — |
| The 4'-thionucleoside phosphamide derivative compound in the present invention + Sorafenib | 1.5 + 30 | 137.33 ± 8.61 | 125.25 ± 20.45 | 94.13 | 5.87 | <0.01 | 1.31 |

"—" means not available.

6.3 Tumor Weight Change

The test results are shown in Table 3. On Day 20 of the treatment, the average tumor weight was 1.19 g and the tumor growth inhibition rate ($TGI_{tumor\ weight}$%) was 38.98% ($T/C_{tumor\ weight}$%=61.02%, p=0.45) when the 4'-thionucleoside phosphamide derivative compound in the present invention was administered alone at a dosage of 1.5 mg/kg; while the average tumor weight was 0.76 g and the tumor growth inhibition rate ($TGI_{tumor\ weight}$%) was 61.03% ($T/C_{tumor\ weight}$%=38.97%, p=0.06) when Sorafenib was administered alone at a dosage of 30 mg/kg.

When the 4'-thionucleoside phosphamide derivative compound in the present invention at a dosage of 1.5 mg/kg was administered in combination with Sorafenib at a dosage of 30 mg/kg for 20 days, the average tumor weight was 0.14 g, and the tumor growth inhibition rate ($TGI_{tumor\ weight}$%) was as high as 92.83% ($T/C_{tumor\ weight}$%=7.17%, p<0.01). The q value calculated according to the Jin's equation was 1.22, indicating that the combination of the two drugs achieved a significant synergistic effect.

TABLE 3

Evaluation of the anti-tumor efficacy on Hep3B cell xenograft

| Group | Dosage mg/kg | Tumor weight (g) | $TGI_{tumor\ weight}$ (%) | $T/C_{tumor\ weight}$ (%) | p value | q value |
|---|---|---|---|---|---|---|
| Vehicle group | — | 1.95 ± 0.31 | — | — | — | — |
| The 4'-thionucleoside phosphamide derivative compound in the present invention | 1.5 | 1.19 ± 0.25 | 38.98 | 61.02 | 0.45 | — |
| Sorafenib | 30 | 0.76 ± 0.17 | 61.03 | 38.97 | 0.06 | — |
| The 4'-thionucleoside phosphamide derivative compound in the present invention + Sorafenib | 1.5 + 30 | 0.14 ± 0.02 | 92.83 | 7.17 | <0.01 | 1.22 |

"—" means not available.

In summary, the combination administration of the 4'-thionucleoside phosphamide derivative compound and Sorafenib can significantly inhibit tumor growth, and this therapeutic effect is significantly superior to that achieved by administration of either of the drugs alone.

Example 2: In Vivo Efficacy on Orthotopic Xenograft of Human Hepatoma Hep3B-Luc Cells This example aimed to evaluate the in vivo efficacy of the pharmaceutical combination of the present invention in a BALB/c nude mouse model with human hepatoma Hep3B-luc cell orthotopic xenografts.

1. Cell Line for the Test

Human hepatoma Hep3B-luc cells were cultured as a monolayer in vitro, and the culture conditions were EMEM culture medium supplemented with 10% Fetal Bovine Serum, and incubation in an incubator at 37° C. and 5% $CO_2$. The cells were subcultured by treatment with routine trypsin-EDTA digestion twice a week. When cell saturation was 80-90%, the number met the requirement, and the cells were harvested and counted.

2. Tumor Cell Inoculation

20 μl of the cell suspension (PBS:Matrigel=1:1) containing about $3×10^6$ Hep3B-Luc cells was injected into the left lobe of the liver of BALB/c-nude mice.

3. Sample Preparation 5 g of sodium carboxymethyl cellulose was weighed and placed in a 1000 mL wide-mouth bottle, 800 mL of ultrapure water was added, and the mixture was stirred to effect a solution, the volume of which was then filled up to 1000 mL, thereby obtaining the vehicle.

An appropriate amount of the 4'-thionucleoside phosphamide derivative compound in the present invention was weighed, a certain amount of the vehicle was added, and a uniform suspension was obtained after mixing.

An appropriate amount of Sorafenib was weighed, and dissolved by adding polyoxyethylene castor oil. Ethanol was added and evenly mixed, followed by addition of physiological saline, thereby obtaining a uniform suspension.

4. Test Method

After inoculation, the tumor growth was assessed by real-time IVIS fluorescence imaging, and mice bearing a tumor with a bioluminescence value of about 1E+8 photons/sec were selected, and randomized into groups (10 mice per group). The dosing volume was 10 mL/kg (in the group treated with the drug combination, the two drugs were administered individually at an interval of 4 hours), and the administration was performed by oral gavage (p.o.) every day for 4 weeks. The tumor volume and tumor weight were measured and recorded by IVIS bioluminescence.

19

5. Test Indexes
(1) Tumor Volume

The anti-tumor effect was evaluated by measuring the bioluminescence value, which reflects the tumor volume. The relative bioluminescence value (RB) was calculated by the measured average bioluminescence value, $RB=B_t/B_0$, wherein $B_0$ is the average bioluminescence value measured at the time of grouping for administration (i.e., Day 0); $B_t$ is the average bioluminescence value measured on Day t. The anti-tumor efficacy was evaluated by tumor growth inhibition $TGI_{fluorescence}$ (%) and $T/C_{fluorescence}$ (%). The equations for calculation are as follows:

$$T/C_{fluorescence}(\%)=T_{RB}/C_{RB}\times100\%;$$

$$TGI_{fluorescence}(\%)=100\%-T/C_{fluorescence}(\%)$$

wherein $T_{RB}$ and $C_{RB}$ are respectively the relative fluorescence values (RB) of the treatment group and vehicle group.

The anti-tumor efficacy was evaluated by $TGI_{fluorescence}\%$ or $T/C_{fluorescence}\%$.

(2) Tumor Weight

The anti-tumor effect was evaluated by tumor weight according to a method same as that described in Example 1.

(3) The Criteria for Determining Synergism were the Same as in Example 1.

6. Test Results
6.1 Tumor Volume Change

The anti-tumor effect was evaluated by detecting the average bioluminescence value which reflects the tumor growth. The test results are shown in Table 4. On Day 28 of the treatment, the average bioluminescence value of tumor was 2.41E+10 photons/sec, and the tumor growth inhibition rate ($TGI_{fluorescence}\%$) was −3.43% ($T/C_{fluorescence}\%=103.43\%$, p=0.62) when the 4'-thionucleoside phosphamide derivative compound in the present invention was administered alone at a dosage of 1.5 mg/kg; while the average bioluminescence value of tumor was 1.51E+10 photons/sec and the tumor growth inhibition rate ($TGI_{fluorescence}\%$) was 35.19% ($T/C_{fluorescence}\%=64.81\%$, p=0.20) when Sorafenib was administered alone at a dosage of 30 mg/kg.

When the 4'-thionucleoside phosphamide derivative compound in the present invention at a dosage of 1.5 mg/kg was administered in combination with Sorafenib at a dosage of 30 mg/kg for 28 days, the average bioluminescence value of tumor was 8.47E+9 photons/sec, and the tumor growth inhibition rate ($TGI_{fluorescence}\%$) was 64.93% ($T/C_{fluorescence}\%=35.07\%$, p<0.01). The q value calculated according to the Jin's equation was 1.97, indicating that the combination of the two drugs achieved a significant synergistic effect.

TABLE 4

Evaluation of the anti-tumor efficacy on orthotopic liver xenograft of Hep3B-luc cells

| Group | Dosage mg/kg | The average bioluminescence value of tumor (photons/sec) | | $TGI_{fluorescence}$ (%) | $T/C_{fluorescence}$ (%) | p value | q value |
| --- | --- | --- | --- | --- | --- | --- | --- |
| | | Day 0 | Day 28 | | | | |
| Vehicle group | — | 1.09E+8 | 2.33E+10 | — | — | — | — |
| The 4'-thionucleoside phosphamide derivative compound in the present invention | 1.5 | 1.09E+8 | 2.41E+10 | −3.43 | 103.43 | 0.62 | — |
| Sorafenib | 30 | 1.09E+8 | 1.51E+10 | 35.19 | 64.81 | 0.20 | — |
| The 4'-thionucleoside phosphamide derivative compound in the present invention + Sorafenib | 1.5 + 30 | 1.13E+8 | 8.47E+9 | 64.93 | 35.07 | <0.01 | 1.97 |

"—" means not available.

6.2 Tumor Weight Change

The test results are shown in Table 5. On Day 28 of the treatment, the average tumor weight was 3.46 g and the tumor growth inhibition rate ($TGI_{tumor\ weight}\%$) was 22.07% ($T/C_{tumor\ weight}\%=77.93\%$, p=0.18) when the 4'-thionucleoside phosphamide derivative compound in the present invention was administered alone at a dosage of 1.5 mg/kg; while the average tumor weight was 1.40 g and the tumor growth inhibition rate ($TGI_{tumor\ weight}\%$) was 68.47% ($T/C_{tumor\ weight}\%=31.53\%$, p<0.001) when Sorafenib was administered alone at a dosage of 30 mg/kg.

When the 4'-thionucleoside phosphamide derivative compound in the present invention at a dosage of 1.5 mg/kg was administered in combination with Sorafenib at a dosage of 30 mg/kg for 28 days, the average tumor weight was 0.37 g, and the tumor growth inhibition rate ($TGI_{tumor\ weight}\%$) was as high as 91.67% (T/C=8.33%, p<0.001). The q value calculated according to the Jin's equation was 1.88, indicating that the combination of the two drugs achieved a significant synergistic effect.

TABLE 5

Evaluation of the anti-tumor efficacy on orthotopic liver xenograft of Hep3B-luc cells

| Group | Dosage mg/kg | Tumor weight (g) | TGI$_{tumor\ weight}$ (%) | T/C$_{tumor\ weight}$ (%) | p value | q value |
|---|---|---|---|---|---|---|
| Vehicle group | — | 4.44 ± 1.91 | — | — | — | — |
| The 4'-thionucleoside phosphamide derivative compound in the present invention | 1.5 | 3.46 ± 1.17 | 22.07 | 77.93 | 0.18 | — |
| Sorafenib | 30 | 1.40 ± 0.82 | 68.47 | 31.53 | <0.001 | — |
| The 4'-thionucleoside phosphamide derivative compound in the present invention + Sorafenib | 1.5 + 30 | 0.37 ± 0.29 | 91.67 | 8.33 | <0.001 | 1.88 |

"—" means not present

In summary, the combination administration of the 4'-thionucleoside phosphamide derivative compound and Sorafenib can significantly inhibit tumor growth, and this therapeutic effect is significantly superior to that achieved by administration of either of the drugs alone.

Example 3: In Vivo Efficacy on Subcutaneous Xenograft of Mouse Colon Cancer MC38 Cells Expressing Humanized PD-L1 (hPD-L1-MC38)

This example aimed to evaluate the in vivo efficacy of the pharmaceutical combination of the present invention in a C57BL/6J mouse model with subcutaneous xenograft of mouse colon cancer hPD-L1-MC38 cells expressing humanized PD-L1.

1. Cell Line for the Test hPD-L1-MC38 cells were cultured as a monolayer in vitro, and the culture conditions were 1640 culture medium supplemented with 10% Fetal Bovine Serum, and incubation in an incubator at 37° C. and 5% $CO_2$. The cells were subcultured by treatment with routine trypsin-EDTA digestion three times a week.

2. Tumor Cell Inoculation and Grouping of Animals 0.1 mL of a PBS resuspension containing $2 \times 10^5$ hPD-L1-MC38 cells was inoculated subcutaneously at the right scapula of each mouse, and the grouping of animals was performed on the day of inoculation.

3. Sample Preparation 5 g of sodium carboxymethyl cellulose was weighed and placed in a 1000 mL wide-mouth bottle, 800 mL of ultrapure water was added, and the mixture was stirred to effect a solution, the volume of which was then filled up to 1000 mL, thereby obtaining the vehicle.

An appropriate amount of the 4'-thionucleoside phosphamide derivative compound in the present invention was weighed, a certain amount of the vehicle was added, and a uniform suspension was obtained after mixing.

An appropriate amount of the hPD-L1 inhibitor (Atezolizumab, trade name: Tecentriq® purchased from Roche Corporation, WHO Pharmaceutical Information (International Nonproprietary Name for Pharmaceutical Substances), Recommended INN: List 74, Vol. 29, No. 3, 2015 (see page 387)) was taken, physiological saline was added to obtain a solution of Tecentriq® at a concentration of 1 mg/mL.

4. Test Method

C57BL/6J mice were inoculated with hPD-L1-MC38 cells, randomized into groups (8 mice per group), and treated by administration on the same day of the inoculation. The dosing volume was 10 mL/kg (in the group treated with the drug combination, the two drugs were administered individually at an interval of 4 hours). The 4'-thionucleoside phosphamide derivative compound in the present invention was administered by oral gavage (p.o.) every day for 4 weeks, and Tecentriq was administered intraperitoneally (i.p.) once every 2 days for 4 weeks. The tumor weight was measured.

5. Test Indexes

The anti-tumor effect was evaluated by the measured tumor weight, and the method of measuring tumor weight and its evaluation were the same as those described in Example 1.

6. Test Results

The test results are shown in Table 6. On Day 28 of the treatment, the average tumor weight was 3.54 g and the tumor growth inhibition rate (TGI$_{tumor\ weight}$%) was 4.84% (T/C$_{tumor\ weight}$%=95.16%, p=0.80) when the 4'-thionucleoside phosphamide derivative compound in the present invention was administered alone at a dosage of 1.5 mg/kg; while the average tumor weight was 2.72 g and the tumor growth inhibition rate (TGI$_{tumor\ weight}$%) was 26.88% (T/C$_{tumor\ weight}$%=73.12%, p=0.19) when Tecentriq was administered alone at a dosage of 10 mg/kg.

When the 4'-thionucleoside phosphamide derivative compound in the present invention at a dosage of 1.5 mg/kg was administered in combination with Tecentriq at a dosage of 10 mg/kg for 28 days, the average tumor weight was 1.80 g, and the tumor growth inhibition rate (TGI$_{tumor\ weight}$%) was 51.61%, (T/C$_{tumor\ weight}$%=48.39%, p<0.01). The q value calculated according to the Jin's equation was 1.70, indicating that the combination of the two drugs achieved a significant synergistic effect.

TABLE 6

Evaluation of anti-tumor efficacy on h-PDL-1-MC38 cell xenograft

| Group | Dosage mg/kg | Tumor weight (g) | TGI$_{tumor\ weight}$ (%) | T/C$_{tumor\ weight}$ (%) | p value | q value |
|---|---|---|---|---|---|---|
| Vehicle group | — | 3.72 ± 0.57 | — | — | — | — |
| The 4'-thionucleoside phosphamide derivative compound in the present invention | 1.5 | 3.54 ± 0.41 | 4.84 | 95.16 | 0.80 | — |

TABLE 6-continued

Evaluation of anti-tumor efficacy on h-PDL-1-MC38 cell xenograft

| Group | Dosage mg/kg | Tumor weight (g) | $TGI_{tumor\ weight}$ (%) | $T/C_{tumor\ weight}$ (%) | p value | q value |
|---|---|---|---|---|---|---|
| Tecentriq | 10 | 2.72 ± 0.44 | 26.88 | 73.12 | 0.19 | — |
| The 4'-thionucleoside phosphamide derivative compound in the present invention + Tecentriq | 1.5 + 10 | 1.80 ± 0.36 | 51.61 | 48.39 | <0.01 | 1.70 |

"—" means not available.

In summary, the combination administration of the 4'-thionucleoside phosphamide derivative compound and Tecentriq can significantly inhibit tumor growth, and this therapeutic effect is significantly superior to that achieved by administration of either of the drugs alone.

In addition to those described herein, according to the foregoing description, various modifications to the present invention would be apparent to those skilled in the art. Such modifications are intended to fall within the scope of the appended claims. Each reference cited herein (including all patents, patent applications, journal articles, books and any other disclosures) are incorporated herein by reference in its entirety.

What is claimed is:

1. A method of therapeutically treating an abnormal cell proliferative disease, comprising administering to a subject a medicament comprising a therapeutically effective amount a 4'-thionucleoside phosphamide derivative, or a pharmaceutically acceptable salt, ester, hydrate, solvate, isomer, any racemate, thereof, or a mixture thereof, and one or more additional therapeutic agents;

wherein the 4'-thionucleoside phosphamide derivative has the structure of formula (I):

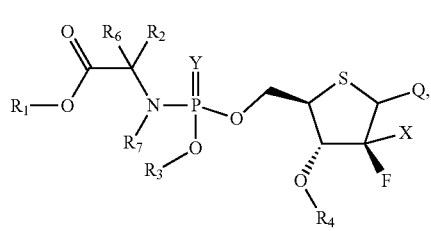

Formula (I)

wherein:

X is hydrogen, $C_{1-6}$ alkyl, halogen, $N_3$, OH, CN or SH;

Y is oxygen or sulfur;

$R_1$, $R_2$, $R_6$, and $R_7$ are each independently selected from the group consisting of hydrogen, optionally substituted $C_{1-10}$ alkyl, optionally substituted cycloalkyl, optionally substituted aryl, optionally substituted heterocyclyl, and optionally substituted heteroaryl, wherein $R_2$ and $R_6$ can be connected to form a 3-8 membered carbocyclic ring which may contain 0-3 heteroatoms selected from the group consisting of N, O, and S, and may be a saturated, unsaturated, or aromatic ring;

$R_3$ is selected from the group consisting of optionally substituted aryl and optionally substituted heteroaryl;

$R_4$ is selected from the group consisting of hydrogen, and optionally substituted $C_{1-10}$ acyl;

Q is a pyrimidine base or a purine base having the following structure:

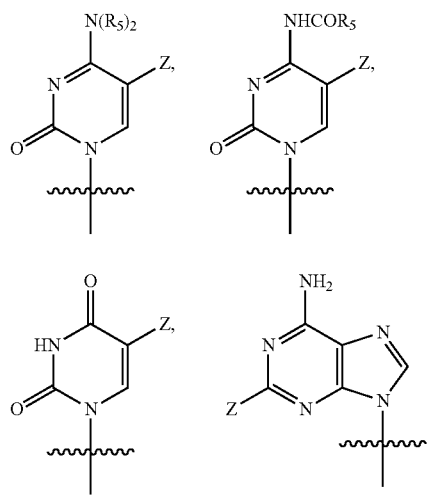

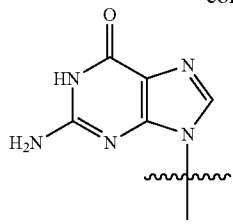

$R_5$, at each occurrence, is independently selected from the group consisting of hydrogen, optionally substituted $C_{1-10}$ alkyl and optionally substituted cycloalkyl; and Z is hydrogen, optionally substituted $C_{1-10}$ alkyl or halogen;

the above expression "optionally substituted" means unsubstituted or substituted with one or more substituents selected from the group consisting of halogen, alkyl, amino, alkylamino, alkoxy, haloalkyl, haloalkoxy, hydroxy, hydroxyalkyl, alkoxyalkyl, amido, sulfonamido, cyano, nitro, nitroso, azido, aldehyde, alkenyl, alkynyl, cycloalkyl, aryl, aralkyl, aryloxy, heteroaryl, heteroaryloxy, acyl, carboxyl, alkylcarbonyl, arylcarbonyl, heteroarylcarbonyl, and carboxylate; and the substituents can be connected to each other to form a 3-8 membered saturated, unsaturated or aromatic ring containing 0-3 heteroatoms selected from the group consisting of N, O, and S;

the one or more additional therapeutic agents are anti-tumor agents, the anti-tumor agent is an anti-tumor antibody agent selected from the group consisting of trastuzumab, rituximab, cetuximab, bevacizumab, nimotuzumab, human endostatin, recombinant human 5 adenovirus, recombinant human tumor necrosis factor, recombinant human P53 adenovirus, iodine (131I) metuximab, nivolumab (Opdivo), pembrolizumab, Avelumab, and Programmed Cell Death-Ligand 1 (PDL-1) antibody; and the abnormal cell proliferative disease is colon cancer, liver cancer or lung cancer.

2. The method according to claim 1, wherein the 4'-thionucleoside phosphamide derivative is selected from the group consisting of the compounds represented by the following formulae:

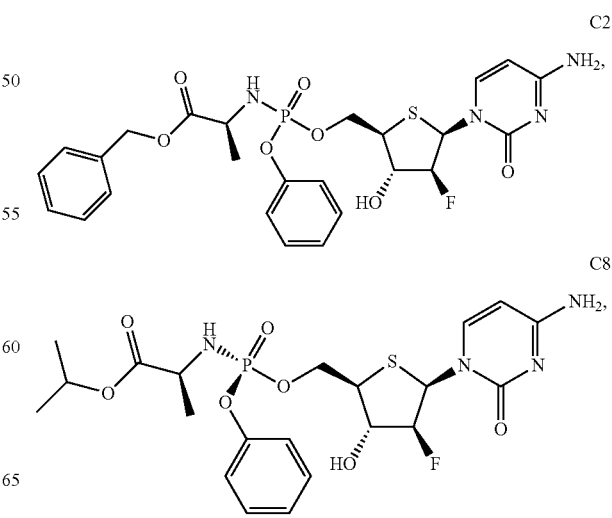

-continued

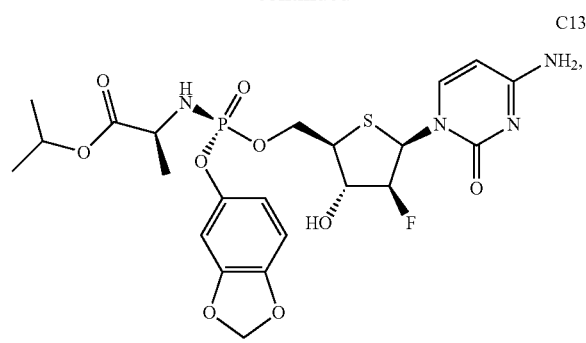
C13

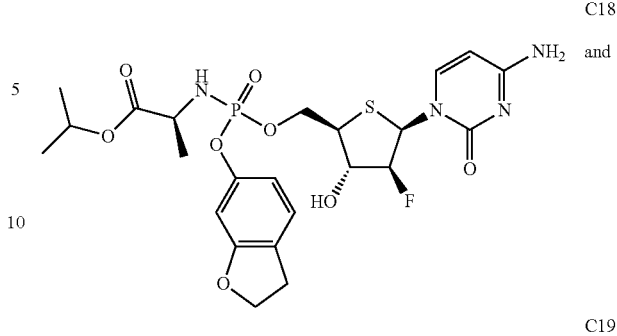
C18 and

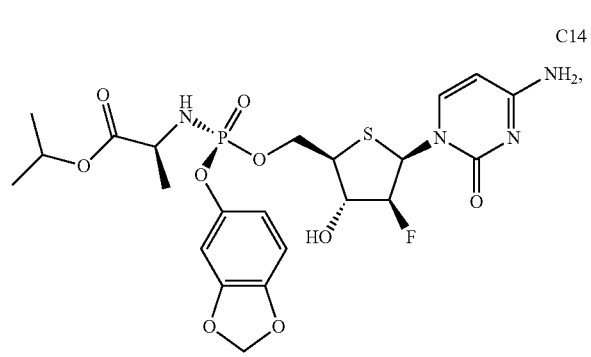
C14

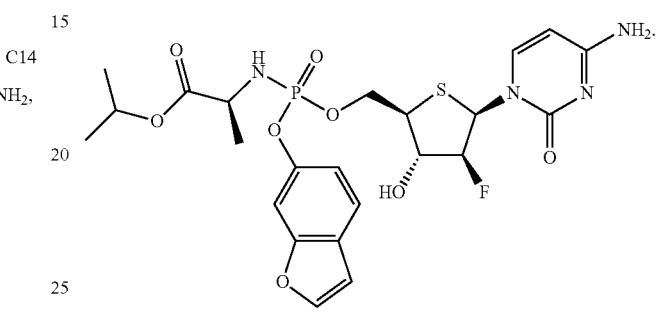
C19

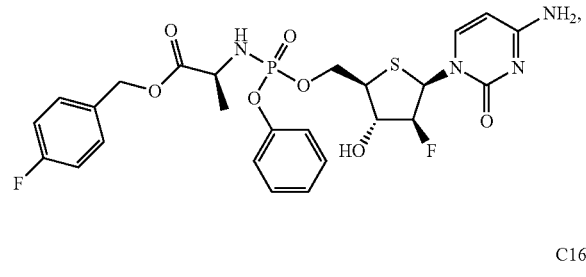
C15

3. The method according to claim 1, wherein the 4'-thio-nucleoside phosphamide derivative is the compound represented by C8:

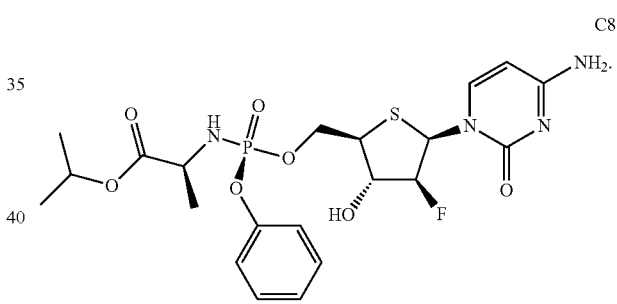
C8

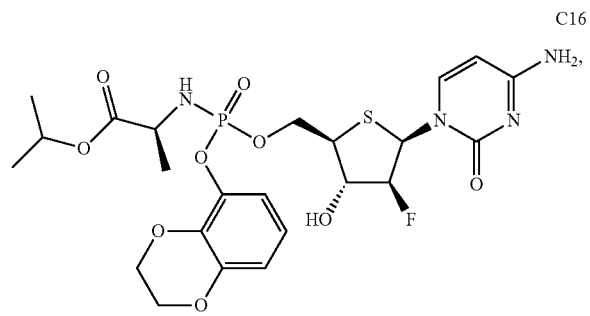
C16

4. The method according to claim 1, wherein the additional therapeutic agent is a PDL-1 antibody.

5. The method according to claim 4, wherein the PDL-1 antibody is Atezolizumab.

6. The method according to claim 4, wherein the PDL-1 antibody is a monoclonal antibody having the following combination of a heavy chain variable region and a light chain variable region: SEQ ID NO:1 and SEQ ID NO:2, SEQ ID NO:3 and SEQ ID NO:4, SEQ ID NO:3 and SEQ ID NO:6, SEQ ID NO:5 and SEQ ID NO:4, or SEQ ID NO:5 and SEQ ID NO:6.

7. The method according to claim 6, wherein the PDL-1 antibody is monoclonal anitbody 5C10, 5C10H1L1, 5C10H2L2, 5C10H1L2, or 5C10H2L1.

8. The method according to claim 4, wherein the PDL-1 antibody comprises a mutated human IgG1 constant region, wherein the heavy chain constant region comprises an N297A mutation according to the EU numbering system.

9. The method according to claim 4, wherein the PDL-1 antibody comprises a mutated human IgG1 constant region, wherein the heavy chain constant region comprises 1, 2 or 3 mutations of L234A, L235A or G237A at positions 234, 235 and 237 according to the EU numbering system.

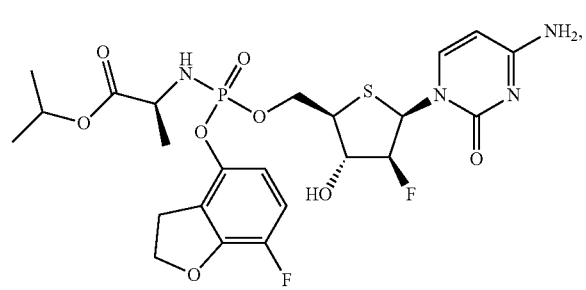
C17

10. The method according to claim 1, wherein the lung cancer is non-small cell lung cancer.

11. The method according to claim 1, wherein one or more dosage units of the 4'-thionucleoside phosphamide derivative and one or more additional therapeutic agents are administered, and the subject is a mammal in need thereof, wherein the 4'-thionucleoside phosphamide derivative, or a pharmaceutically acceptable salt, ester, hydrate, solvate, isomer, any racemate, thereof, or a mixture thereof and one or more additional therapeutic agents administered simultaneously, sequentially or alternately.

12. The method according to claim 1, wherein the subject is human.

* * * * *

UNITED STATES PATENT AND TRADEMARK OFFICE
CERTIFICATE OF CORRECTION

PATENT NO.         : 11,266,674 B2
APPLICATION NO.    : 16/627897
DATED              : March 8, 2022
INVENTOR(S)        : Hongmei Song Page 1 of 1

It is certified that error appears in the above-identified patent and that said Letters Patent is hereby corrected as shown below:

In the Claims

Column 29, Claim 1, Lines 4-5:
"effective amount a" should read: --effective amount of a--

Column 32, Claim 7, Line 56:
"anitbody" should read: --antibody--

Column 33, Claim 11, Line 9:
"racemate, thereof," should read: --racemate thereof,--

Column 33, Claim 11, Line 10:
"agents administered" should read: --agents are administered--

Signed and Sealed this
Thirty-first Day of October, 2023

Katherine Kelly Vidal
*Director of the United States Patent and Trademark Office*

SEQUENCE LISTING

```
<160> NUMBER OF SEQ ID NOS: 6

<210> SEQ ID NO 1
<211> LENGTH: 120
<212> TYPE: PRT
<213> ORGANISM: Artificial Sequence
<220> FEATURE:
<223> OTHER INFORMATION: amino acid sequence of the heavy chain variable
      region of monoclonal antibody 5C10

<400> SEQUENCE: 1

Gln Val Gln Leu Lys Glu Ser Gly Pro Gly Leu Val Ala Pro Ser Gln
1               5                   10                  15

Asn Leu Ser Ile Thr Cys Thr Val Ser Gly Phe Ser Leu Ser Asn Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Ala Thr Asn Tyr Asn Ser Ala Phe Met
    50                  55                  60

Ser Arg Leu Ser Ile Ser Arg Asp Asn Ser Lys Ser Gln Val Phe Leu
65                  70                  75                  80

Lys Met Asn Ser Leu Gln Thr Asp Asp Thr Ala Ile Tyr Tyr Cys Val
                85                  90                  95

Arg Asp Ser Asn Tyr Arg Tyr Asp Glu Pro Phe Thr Tyr Trp Gly Gln
            100                 105                 110

Gly Thr Leu Val Thr Val Ser Ala
        115                 120

<210> SEQ ID NO 2
<211> LENGTH: 106
<212> TYPE: PRT
<213> ORGANISM: Artificial Sequence
<220> FEATURE:
<223> OTHER INFORMATION: amino acid sequence of the light chain variable
      region of monoclonal antibody 5C10

<400> SEQUENCE: 2

Asp Ile Leu Leu Thr Gln Ser Pro Ala Ile Leu Ser Val Ser Pro Gly
1               5                   10                  15

Glu Arg Val Ser Leu Ser Cys Arg Ala Ser Gln Ser Ile Gly Thr Asn
            20                  25                  30
```

```
Ile His Trp Phe Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Ser Asn Ser Trp Pro Tyr
                 85                  90                  95

Thr Phe Gly Gly Gly Thr Lys Leu Glu Ile
                100                 105

<210> SEQ ID NO 3
<211> LENGTH: 120
<212> TYPE: PRT
<213> ORGANISM: Artificial Sequence
<220> FEATURE:
<223> OTHER INFORMATION: amino acid sequence of the heavy chain variable
      region of monoclonal antibody 5C10H1L1

<400> SEQUENCE: 3

Gln Val Gln Leu Gln Glu Ser Gly Pro Gly Leu Val Lys Pro Ser Glu
 1               5                  10                  15

Asn Leu Ser Ile Thr Cys Thr Val Ser Gly Phe Ser Leu Ser Asn Tyr
                20                  25                  30

Asp Ile Ser Trp Ile Arg Gln Pro Pro Gly Lys Gly Leu Glu Trp Leu
        35                  40                  45

Gly Val Ile Trp Thr Gly Gly Ala Thr Asn Tyr Asn Pro Ala Phe Lys
 50                  55                  60

Ser Arg Leu Thr Ile Ser Arg Asp Asn Ser Lys Ser Gln Val Ser Leu
 65                  70                  75                  80

Lys Met Ser Ser Leu Gln Ala Ala Asp Thr Ala Val Tyr Tyr Cys Val
                 85                  90                  95

Arg Asp Ser Asn Tyr Arg Tyr Asp Glu Pro Phe Thr Tyr Trp Gly Gln
                100                 105                 110

Gly Thr Leu Val Thr Val Ser Ser
        115                 120

<210> SEQ ID NO 4
<211> LENGTH: 107
<212> TYPE: PRT
<213> ORGANISM: Artificial Sequence
<220> FEATURE:
<223> OTHER INFORMATION: amino acid sequence of the light chain variable
      region of monoclonal antibody 5C10H1L1

<400> SEQUENCE: 4

Glu Ile Val Leu Thr Gln Ser Pro Asp Thr Leu Ser Val Thr Pro Lys
 1               5                  10                  15

Glu Lys Val Thr Leu Thr Cys Arg Ala Ser Gln Ser Ile Gly Thr Asn
                20                  25                  30

Ile His Trp Phe Gln Gln Arg Pro Gly Gln Ser Pro Lys Leu Leu Ile
        35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Thr Ile Asn Ser Val Glu Ala
 65                  70                  75                  80

Glu Asp Ala Ala Thr Tyr Tyr Cys Gln Gln Ser Asn Ser Trp Pro Tyr
                 85                  90                  95
```

```
Thr Phe Gly Gln Gly Thr Lys Leu Glu Ile Lys
            100                 105
```

<210> SEQ ID NO 5
<211> LENGTH: 120
<212> TYPE: PRT
<213> ORGANISM: Artificial Sequence
<220> FEATURE:
<223> OTHER INFORMATION: amino acid sequence of the heavy chain variable
      region of monoclonal antibody 5C10H2L2

<400> SEQUENCE: 5

```
Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Asn Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Ala Thr Asn Tyr Asn Pro Ala Leu Lys
    50                  55                  60

Ser Arg Leu Thr Ile Ser Arg Asp Asn Ser Lys Asn Gln Val Ser Leu
65                  70                  75                  80

Lys Met Ser Ser Val Thr Ala Ala Asp Thr Ala Val Tyr Tyr Cys Val
                85                  90                  95

Arg Asp Ser Asn Tyr Arg Tyr Asp Glu Pro Phe Thr Tyr Trp Gly Gln
            100                 105                 110

Gly Thr Leu Val Thr Val Ser Ser
        115                 120
```

<210> SEQ ID NO 6
<211> LENGTH: 107
<212> TYPE: PRT
<213> ORGANISM: Artificial Sequence
<220> FEATURE:
<223> OTHER INFORMATION: amino acid sequence of the light chain variable
      region of monoclonal antibody 5C10H2L2

<400> SEQUENCE: 6

```
Glu Ile Val Leu Thr Gln Ser Pro Asp Thr Leu Ser Val Thr Pro Lys
1               5                   10                  15

Glu Lys Val Thr Leu Thr Cys Arg Ala Ser Gln Ser Ile Gly Thr Asn
            20                  25                  30

Ile His Trp Phe Gln Gln Lys Pro Gly Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ala
65                  70                  75                  80

Glu Asp Ala Ala Thr Tyr Tyr Cys Gln Gln Ser Asn Ser Trp Pro Tyr
                85                  90                  95

Thr Phe Gly Gln Gly Thr Lys Leu Glu Ile Lys
            100                 105
```